United States Patent [19]

Rosenman

[11] Patent Number: 5,728,116
[45] Date of Patent: Mar. 17, 1998

[54] SPIRAL SURGICAL TACK

[75] Inventor: Daniel C. Rosenman, Hazlet, N.J.

[73] Assignee: Ethicon, Inc., Somerville, N.J.

[21] Appl. No.: 746,023

[22] Filed: Nov. 5, 1996

Related U.S. Application Data

[62] Division of Ser. No. 715,800, Mar. 19, 1996, which is a continuation of Ser. No. 390,327, Feb. 17, 1995, abandoned, which is a continuation of Ser. No. 180,722, Jan. 13, 1994, abandoned.

[51] Int. Cl.$^6$ ..................................................... A61B 17/08
[52] U.S. Cl. ........................... 606/151; 606/232; 606/213
[58] Field of Search .................................. 606/151, 157, 606/158, 213, 222, 232, 73, 75, 143; 623/13; 411/392, 425; 24/711.2, 711.3

[56] References Cited

U.S. PATENT DOCUMENTS

| | | | |
|---|---|---|---|
| D. 366,113 | 1/1996 | Morgan | D24/145 |
| 2,033,039 | 3/1936 | Limbert | 24/711.3 |
| 2,230,349 | 2/1941 | Eaton et al. | 52/489.1 |
| 3,882,756 | 5/1975 | Sauer et al. | 411/426 |
| 4,756,653 | 7/1988 | Berger | 411/426 |
| 4,815,909 | 3/1989 | Simons | 411/392 |
| 4,873,976 | 10/1989 | Schreiber . | |
| 4,895,148 | 1/1990 | Bays et al. . | |
| 4,976,715 | 12/1990 | Bays et al. . | |
| 5,246,441 | 9/1993 | Ross et al. . | |
| 5,258,000 | 11/1993 | Gianturco . | |
| 5,263,974 | 11/1993 | Matsutani et al. | 606/222 |
| 5,342,397 | 8/1994 | Guido | 606/222 |
| 5,464,421 | 11/1995 | Wortrich . | |
| 5,582,616 | 12/1996 | Boldue et al. . | |

*Primary Examiner*—Jeffrey A. Schmidt
*Assistant Examiner*—Patrick W. Rasuhe
*Attorney, Agent, or Firm*—Emil Richard Skula

[57] ABSTRACT

A surgical tack for use in surgical procedures. The surgical tack has a base member and a distally extending spiral member having a distal piercing point. The spiral member forms a spiral. The tack may be used to fasten tissue, sutures, or medical devices to tissue.

2 Claims, 7 Drawing Sheets

SPIRAL SURGICAL TACK

This is a division of application Ser. No. 08/715,800, filed Sep. 19, 1996, which is hereby incorporated by reference which is a continuation of application Ser. No. 08/390, 327, filed Feb. 17, 1995, now abandoned, which is a continuation of application Ser. No. 08/180,722, filed Jan. 13, 1994, now abandoned.

TECHNICAL FIELD

The field of art to which this invention relates is surgical devices, more particularly, surgical tacks.

BACKGROUND ART

Surgical staples are well known in the surgical arts. These staples have been widely used by surgeons to approximate incisions and wounds. Surgical staples have proven to be a useful alternative available to the medical practitioner in lieu of conventional sutures.

Surgical staples are often used in various surgical procedures. For example, when performing a surgical procedure to repair an inguinal hernia, one common technique is to affix a biocompatible surgical mesh over the site of the inguinal hernia. This is typically done by stapling the surgical mesh to the tissue and muscle surrounding the site of the hernia. The staples used in this procedure are, typically, conventional metal staples made from stainless steel, titanium, tantalum, or the like. There are several disadvantages associated with the use of metal staples in such a procedure. One obvious disadvantage is that the metal staples may remain inside of the patient indefinitely. In addition, it is not uncommon for a nerve to be entrapped and compressed by a metal staple. It is believed that this may cause residual pain in the patient. In order to alleviate such pain, a subsequent operation may be required to remove and/or replace the staples.

Another disadvantage of conventional staples is that the holding power of such conventional staples is limited by the size of the staple wire and the stiffness and mechanical properties of the material. A larger and/or stiffer metal staple is harder to bend around an anvil of a conventional surgical apparatus, and therefore limited in its strength. In some cases conventional metal staples may pull out of tissue because they are not strong or large enough.

The use of absorbable staples may help to overcome these problems and eliminate the need for additional surgery since, for example, an absorbable staple would absorb over time, thereby relieving any pressure upon a compressed nerve. Although absorbable staples are known in this art, such staples typically require access to both sides of a tissue site since they typically consist of an upper section having a crown and legs and a lower receiver. The lower receiver engages and locks the legs of the staple. Therefore, the absorbable staples known in the art are typically not usable in surgical procedures such as repair of an inguinal hernia where there is only access to one side of the tissue. Another type of absorbable staple which does not require a lower receiver is a three-piece staple described in commonly assigned, co-pending U.S. patent application Ser. No. 146, 755 filed on Nov. 2, 1993 which is incorporated by reference.

There is a need in this art for surgical fastening devices which do not require a second separate piece or receiver to lock or maintain the fastener in place in tissue, which can be applied and secured from one side of a tissue site in an endoscopic or open surgical procedure, and which overcomes the disadvantages associated with conventional surgical staples.

DISCLOSURE OF THE INVENTION

Therefore, it is an object of the present invention to provide a surgical fastener which does not require an additional member to lock or maintain the fasteners in tissue.

It is a further object of the present invention to provide a surgical tack which easily attaches either tissue to tissue, sutures to tissue, or surgical devices such as mesh to tissue.

It is yet a further object of the present invention to provide a surgical tack which can be used for attachment wherein the tack is inserted from a single side of the tissue.

It is still yet a further object of the present invention to provide a method of attaching tissue using a surgical tack.

Accordingly, a surgical tack for use in surgical procedures is disclosed. The surgical tack comprises a base member having a top and a bottom. An optional suture mounting member may extend from the base member. A member extends from the bottom of the base member. The member is formed into a spiral having a longitudinal axis and a plurality of loops separated by spaces. The member has a proximal end and a distal end. Preferably, the member has at least one outwardly extending edge. The member has a piercing point extending from its distal end. The piercing point may extend substantially parallel to the longitudinal axis or may be angulated with respect thereto. The member may have various types of cross-sections including a semi-cylindrical cross-section, a triangular cross-section, a parabolic cross-section, and a rectangular cross-section. The spiral consists of at least one coil. The coils may have a circular configuration or square, triangular or polygonal configurations. Optionally, various shaped cavities may be formed into the top surface of the base member to facilitate driving of the tack, e.g., slots, etc.

Yet another aspect of the present invention is a method of fastening tissue. The method comprises inserting the above-described tack into one side of the tissue. The tack may be used to fasten tissue to tissue, sutures to tissue, or medical devices to tissue including surgical meshes.

Other features and advantages of the invention will become more apparent from the following description and accompanying drawings.

BEST MODE FOR CARRYING OUT THE INVENTION

Figure 1:
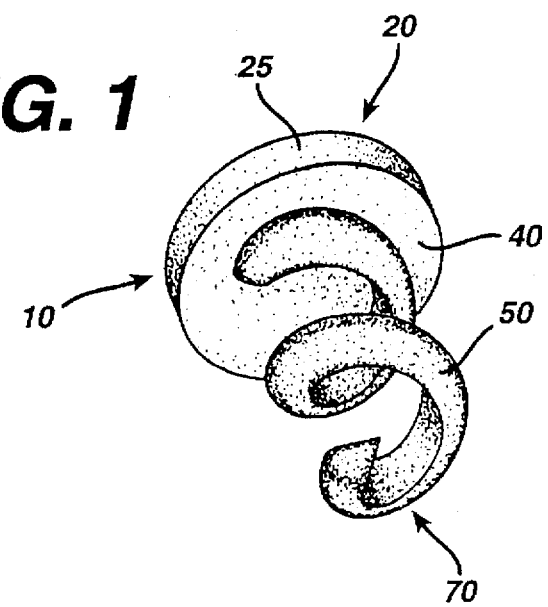
FIG. 1 is a perspective view of the surgical tack of the present invention.
Figure 2:
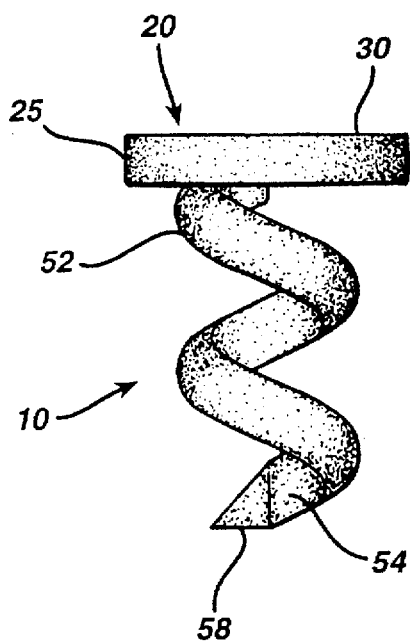
FIG. 2 is a side view of the surgical tack of the present invention.

The surgical tacks of the present invention are illustrated in FIGS. 1–19. Referring first to FIGS. 1–4, the tack 10 is seen to have a base member 20. The base member 20 has top surface 30 and bottom surface 40 and side surfaces 25 connecting the top surface 30 and the bottom surface 40. The base member 20 preferably has a circular disk-like shape, however, other shapes may be utilized including rectangular, square, hexagonal, and polygonal. The base member 20 may be solid or have a hole through it to facilitate the manufacture of a distally extending spiral. The top surface 30 of the base member 20 may have features incorporated therein to facilitate the driving of the tack (see FIGS. 8–11). These features may consist of cavities such as cavities 31, 32, 33, and 34, to accept slotted screw drivers, Allen, Phillips, or Torx screw drivers, respectively, or square or other tools to impart rotation to the tack 10. A distally extending spiral member 50 is seen to extend down from the bottom surface 40 of the base member 30. The distally extending member 50 preferably is shaped to form a spiral 60 having coils 65 of constant size, although the size of the coils may vary, if desired, along the longitudinal length of the spiral. The coils 65 are seen to be separated by gaps which are constant or which vary along the longitudinal axis of the spiral. Member 50 is seen to have proximal end 52 and distal end 54.

Figure 4:
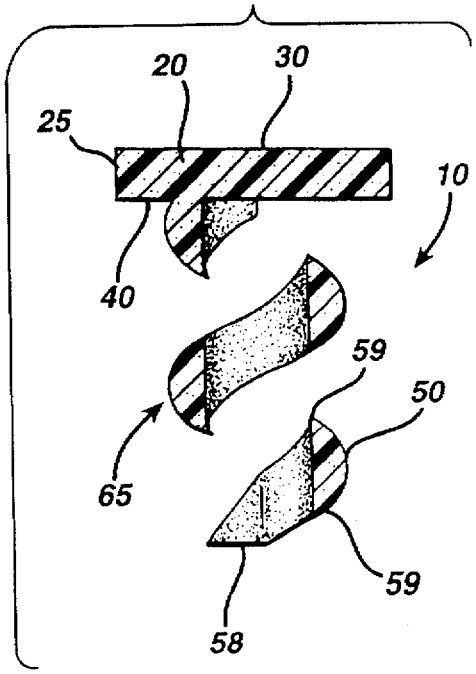
FIG. 4 is a cross-sectional view of the surgical tack of FIG. 3 taken along view line 4—4.
Figure 3:
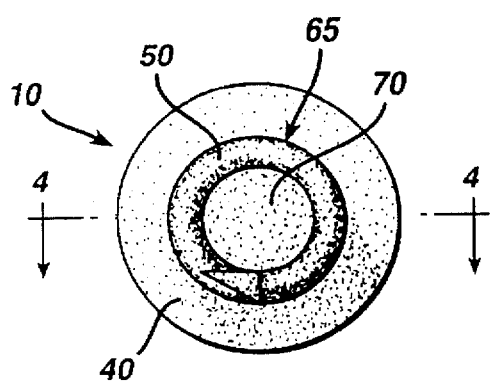
FIG. 3 is a bottom view of the surgical tack of the present invention illustrating a member extending distally from the bottom of the base member to form a spiral.

Extending from the distal end 54 is the piercing tip 58. The piercing tip 58 may have a conventional sharp piercing point configuration sufficient to effectively penetrate through tissue. The piercing tip 58 may also have a blunt configuration effective to pierce tissue. The piercing point 58 may be aligned parallel to the longitudinal axis of the spiral 60, or be pointed obliquely off the axis of the spiral to facilitate penetration of tissue. The member 50 or tip 58 may have one or a plurality of barbs that increase the holding power of the tack in tissue. The member 50 is seen to have, preferably, at least one edge 59. Referring to FIG. 4, the member 50 is seen to have a substantially semi-cylindrical cross-sectional configuration with two outer edges 60. As seen in FIGS. 3 and 4, a passage 70 is contained within the spiral 60.

Figure 5:
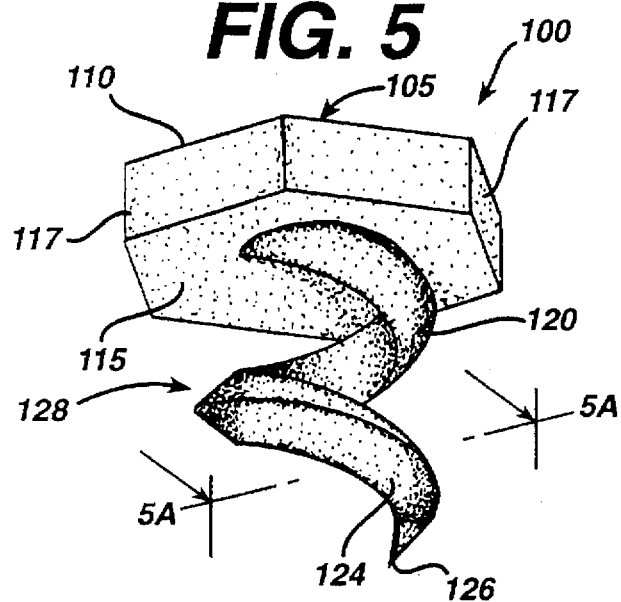
FIG. 5 is an illustration of a perspective view of an alternate embodiment of the surgical tack of the present invention having a hexagonal base member.
Figure 5A:
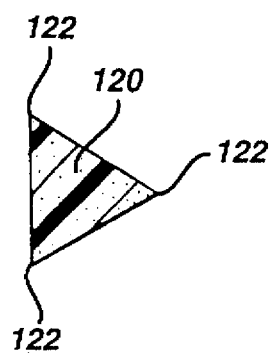
FIG. 5A is a cross-sectional view of the spiral member of the tack of FIG. 5 taken along view line 5A—5A illustrating the triangular cross-section of the member.

An alternate embodiment of the surgical tack 10 of the present invention is seen in FIG. 5. The tack 100 is seen to have a hexagonal base member 105 having top 110 and bottom surface 115. Side surfaces 117 connect top surface 105 with bottom surface 115. Distally extending spiral member 120 is seen to extend downwardly from the bottom surface 115 forming spiral 128. As seen in FIG. 5A, the member 120 is seen to have a triangular cross-section and three outer edges 122. Point 126 is seen to extend from the distal end 124 of the member 120.

Figure 6:
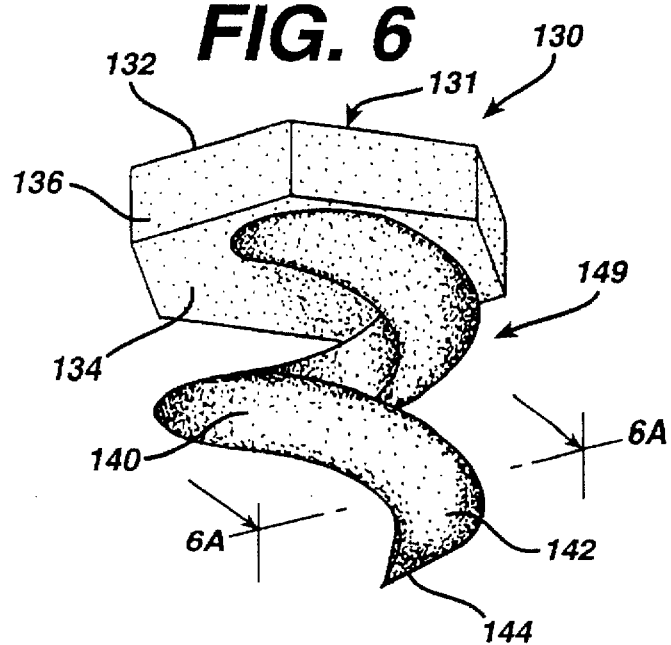
FIG. 6 is a perspective view of an alternate embodiment of a surgical tack of the present invention.
Figure 6A:
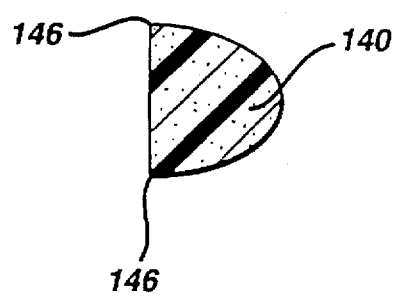
FIG. 6A is a cross-sectional view of the spiral member of the tack of FIG. 6 taken along view lines 6A—6A illustrating a parabolic cross-section of the member.

Yet another embodiment of the present invention is seen in FIG. 6. The tack 130 is seen to have a hexagonal base member 131 having top surface 132, bottom surface 134 and connecting side surfaces 136. Extending distally from the bottom surface 134 of the base member 131 is the spiral member 140 forming spiral 149. Member 140 is seen to have distal end 142 and piercing point 144 extending from distal end 142. Referring to FIG. 6A, the member 140 is seen to have a substantially parabolic cross-section having outer edges 146.

Figure 7:
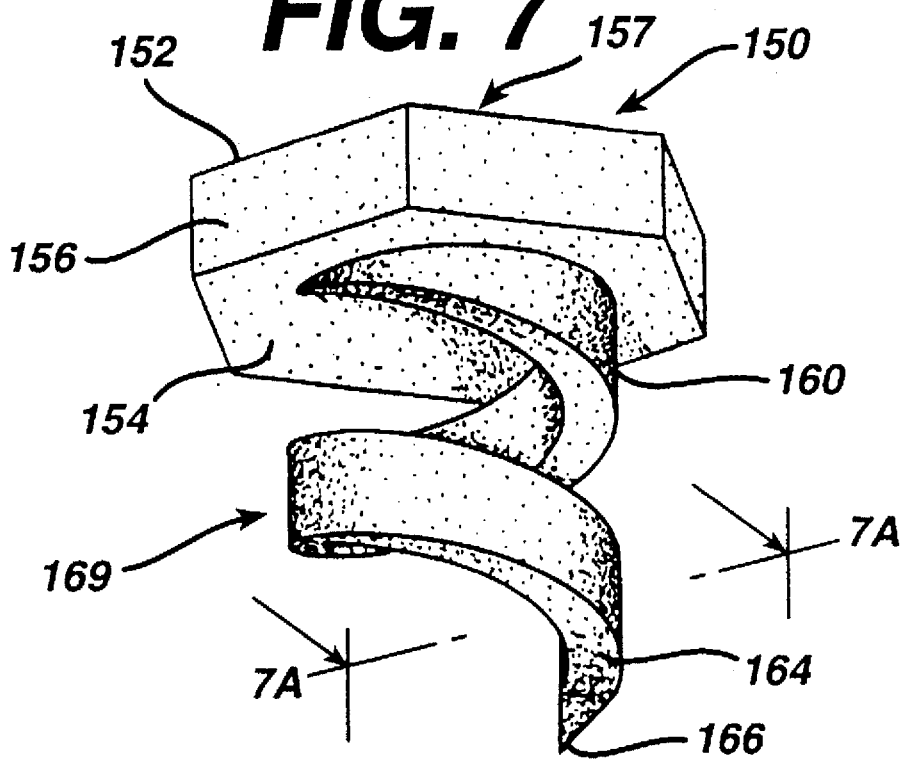
FIG. 7 is a perspective view of an alternate embodiment of the tack of the present invention.
Figure 7A:
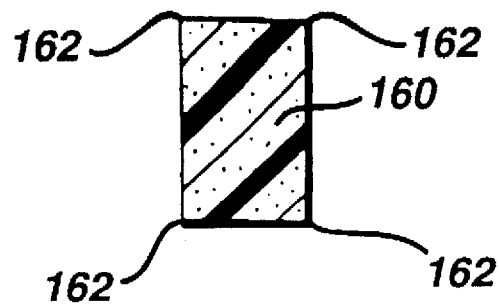
FIG. 7A is a cross-sectional view of the spiral member of the tack of FIG. 7 illustrating a rectangular cross-section.
Figure 8:
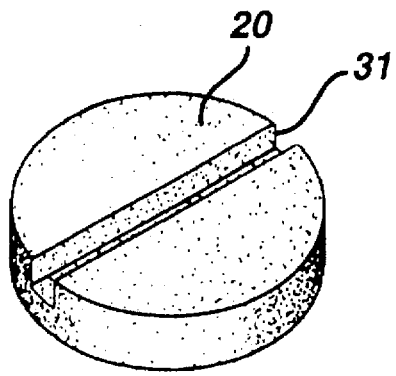
FIG. 8 is a perspective view of the base member of the tack of FIG. 1 having a slotted cavity for receiving the tip of a conventional screw driver.
Figure 9:
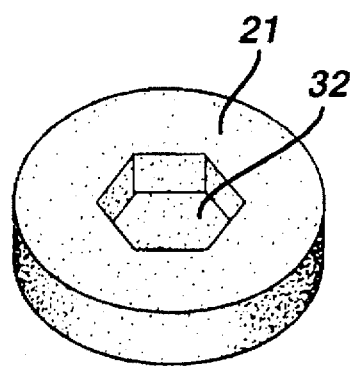
FIG. 9 is a perspective view of the base member of the tack of FIG. 1 having a cavity for receiving the tip of an Allen wrench.
Figure 10:
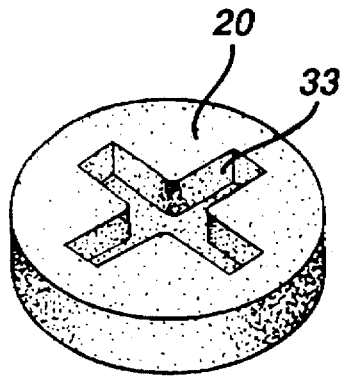
FIG. 10 is a perspective view of the base member of the tack of FIG. 1 having a cavity for receiving the tip of a Phillips screw driver.
Figure 11:
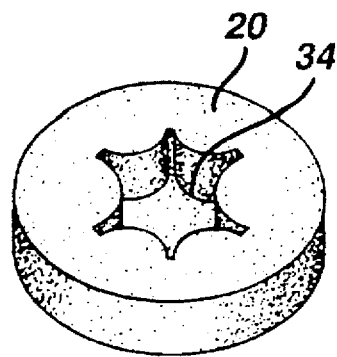
FIG. 11 is a perspective view of the base member of the tack of FIG. 1 having a cavity for receiving the tip of a Torx screw driver.

Another embodiment of the tack of the present invention is seen in FIG. 7. The tack 150 is seen to have base member 151. The base member 151 is seen to be substantially hexagonally shaped. The base member 150 is seen to have upper surface 152, lower surface 154 and side connecting surfaces 156. Extending distally from the bottom 154 of the base member 150 is the spiral member 160 forming spiral 169. The member 160 is seen to have edges 162, distal end 164, and point 166 extending from the distal end 164. Referring to FIG. 7A, the member 160 is seen to have a generally substantially rectangular cross-section having outer edges 166.

Figure 12:
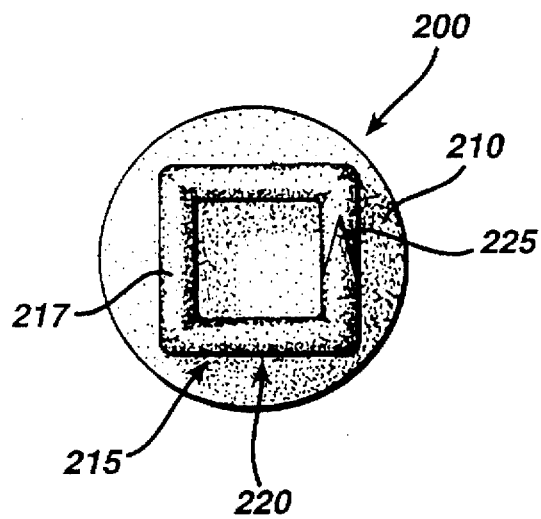
FIG. 12 is a bottom view of an alternate embodiment of the tack of the present invention wherein the spiral has square coils.

The spiral member of the tacks of the present invention may be formed into various shaped spirals. For example, the tack 10 of FIG. 1 is seen to have a spiral 60 which is helical in shape having circular coils of constant diameter. In addition, the spirals of the tacks of the present invention may have various other geometric configurations. For example, FIG. 12 illustrates a tack 200 having a base member 210 and a spiral member 215 formed into a spiral 217 wherein the coils 220 have a square configuration. The piercing point 225 is directed perpendicular to the longitudinal axis of spiral 217.

Figure 13:
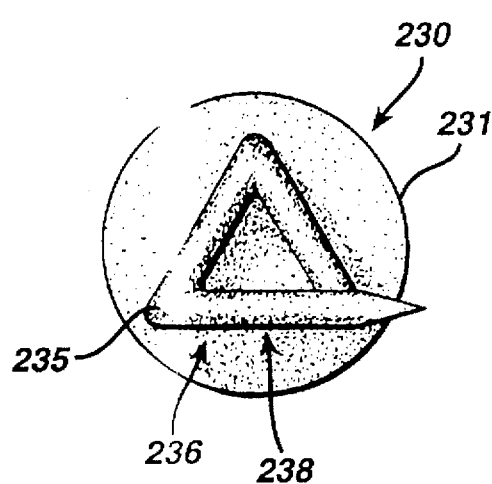
FIG. 13 is a bottom view of an alternate embodiment of the tack of the present invention wherein the spiral has triangular coils.
Figure 14:
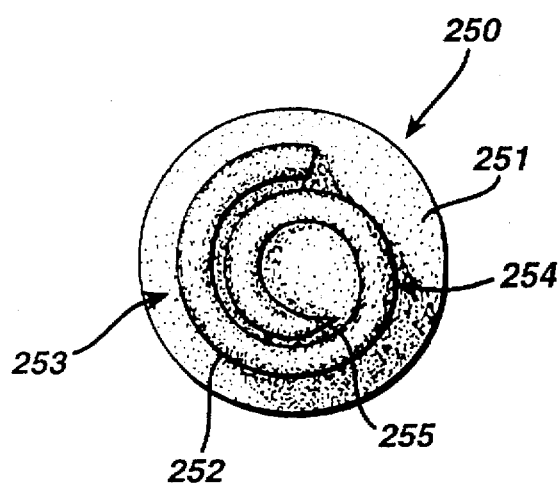
FIG. 14 is a bottom view of an alternate embodiment of the tack of the present invention wherein the spiral has circular coils which vary in diameter along the longitudinal axis of the spiral.
Figure 15:
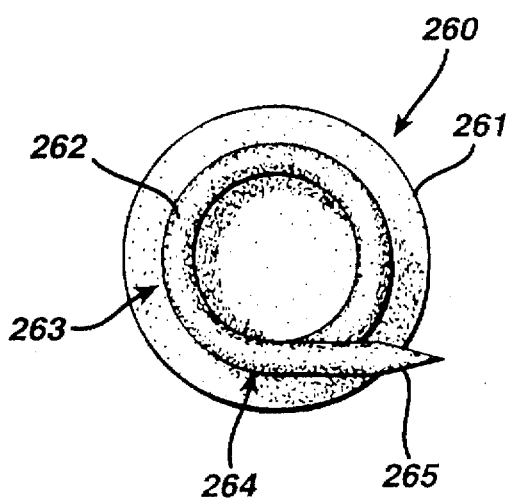
FIG. 15 is a bottom view of an alternate embodiment of the tack of the present invention wherein the spiral member is formed into a spiral having circular coils and the piercing point is perpendicular to the longitudinal axis of the spiral.

Referring to FIG. 13, a tack 230 is seen to have a base member 231 and a distally extending spiral member 235 forming a spiral 236 having triangularly shaped coils 238. The piercing point 240 is seen to extend perpendicular to the longitudinal axis of the coil 236. Another embodiment of a spiral is seen in FIG. 14. The tack 250 is seen to have base member 251 and distally extending spiral member 252 forming spiral 253 having coils 254 which are generally circular in configuration and decrease in diameter along the longitudinal length of the spiral 253. The point 255 is seen to be generally aligned with the longitudinal axis of spiral 253. Referring to FIG. 15, an alternate embodiment of the tack 10 of FIG. 1 is illustrated. The tack 260 is seen to have base member 261 and downwardly extending spiral member 262 forming spiral 263 having coils 264 of circular configuration and constant diameter. The piercing point 265 is seen to be directed substantially perpendicular to the longitudinal axis of the spiral 263.

Figure 16:
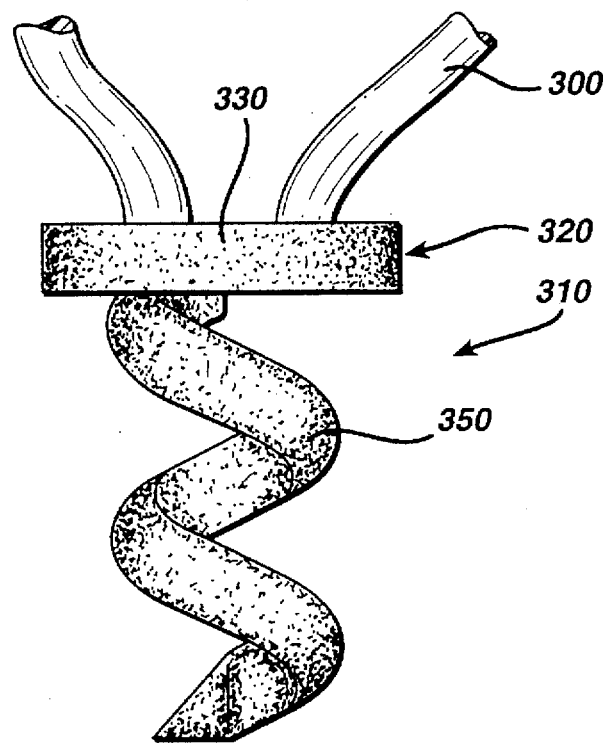
FIG. 16 is a side view of the tack of FIG. 1 having the ends of surgical sutures mounted therein.

Sutures may be affixed to the tacks of the present invention in various manners. Referring to FIG. 16, a tack 310 is seen to have a base member 320, having top 330 and downwardly extending spiral member 350. Two ends of a suture are seen to be mounted in the base member 320 extending upward from the top 330 of the base member 320. The sutures may be mounted in conventional manners including co-molding, bonding, mechanical fasteners, adhesives, welding and the like.

Figure 17:
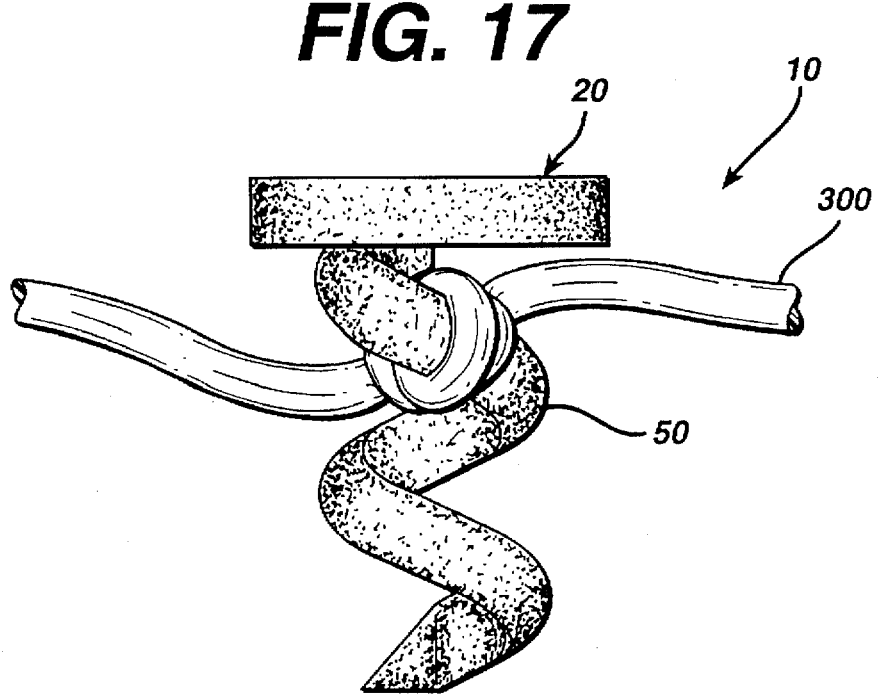
FIG. 17 is a side view of the tack of FIG. 1 illustrating a surgical suture tied to the spiral member.

An alternate suture mounting configuration is seen in FIG. 17. In FIG. 17, a suture 300 is seen to be tied about the proximal end of distally extending spiral member 50 of a tack 10 of the present invention adjacent to the base member 20.

Figure 18:
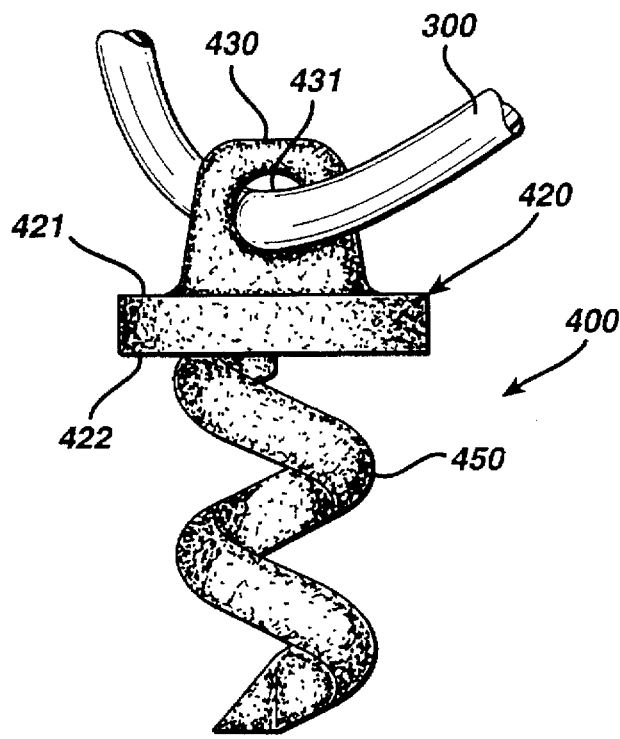
FIG. 18 illustrates an alternate embodiment of the tack of the present invention having a suture mounting means extending from the top of the base member.
Figure 19:
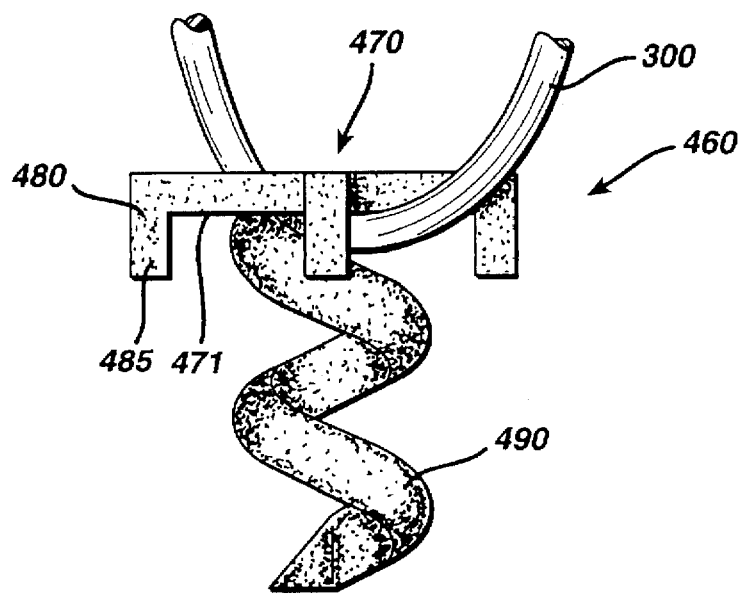
FIG. 19 illustrates an alternate embodiment of the tack of the present invention having a base member having crossed beam members which can also be used to mount a suture.

An alternate configuration for mounting a suture to a tack of the present invention is seen in FIG. 18. A tack 400 is illustrated having base number 420 having a top surface 421 and a bottom surface 422. Extending downwardly from the bottom surface 422 is a spiral member 450. Extending upwardly from surface 421 of the base number 420 is the suture mounting member 430 having suture receiving hole 431. The suture 300 is threaded through suture receiving hole 431. Yet another embodiment of a tack having a suture mounting configuration is seen in FIG. 19. The tack 460 is seen to have a base number 470 consisting of outwardly extending members 480 each having distally extending end sections 485. The tack is seen to have distally extending spiral member 490 extending from the bottom surface 481 of the base member 470. Suture 300 is mounted about the base number 470 and is contained by the downwardly extending retention members 485.

The surgical tacks of the present invention may be used to approximate tissues, to hold a medical device to the surface of tissue including, for example, a surgical mesh, or to anchor tissue to an anatomic site. The tacks of the present invention can be manufactured in small sizes useful in endoscopic surgical techniques. The tacks resist large removal forces. In addition, the tacks can be applied when the surgeon has access to only one side of a tissue site. The tacks of the present invention tend to be atraumatic because unlike staples, they do not compress tissue and they only puncture at one site per fastener versus typically two per site for conventional staples and fasteners. It is known that the use of staples, which squeeze tissue when they are applied or fired, may in certain instances cause ischemia, with resultant necrosis depending upon the pressure exerted by the staple. In addition, most staples are made of non-absorbable materials and remain behind even after the critical healing period.

The tacks of the present invention may be manufactured from absorbable or non-absorbable materials. It is particularly preferred to manufacture the tacks of the present invention from absorbable materials which are absorbed by the body over the course of the healing process thereby eliminating the fastener when it is no longer needed to perform its function approximating or fastening tissue.

The tacks of the present invention, such as tack 10, are used in the following manner. The tack is grasped by an appropriate grasping instrument, such as a conventional surgical grasper, screw driver, nut driver, allen wrench, or endosurgical grasper or may even be applied by hand. The point 58 of the tack 10 is pressed against the outer surface of the tissue. Then, the tack is rotated to set the curved member into the tissue. The tack may be used on various types of tissues ranging from soft muscle, fascia, or fat to hard ligaments and tendons.

The tacks of the present invention 10 will have a spiral member having a cross-sectional configuration sufficiently large to effectively anchor the tack 10 in tissue when formed into a spiral. For example, the tack 10 may have a spiral member 50 having a circular cross-section with a diameter of about 0.010 inches to about 0.075 inches. The length of the spiral and the size of the coils will depend upon the particular application and the characteristics of the materials of construction. The mechanical characteristics of the materials of construction, e.g., stiffness, will be sufficient to effectively enable the tack to penetrate tissue without deforming. The major dimension of the coils of the spiral will be appropriate for the tissue in which the tack is being anchored, and will be sufficient to effectively provide the required holding power of the tack, and may depend upon the method with which the tack is being applied. For example, the diameter of the coils may vary from about 0.125 inches to about 0.250 inches. The length of the spiral and the number of coils of the spiral will depend on the holding power required and the depth of tissue in which the tack will be anchored as well as the type of tissue. The number of coils can be any amount greater than one-half. One skilled in the art will readily appreciate minimal routine experimentation will readily lead to a determination of the optimal spiral length, coil major dimensions, and number of coils for each particular application.

The surgical tacks of the present invention may be made from either conventional bioabsorbable materials or conventional non-absorbable materials, combinations thereof and equivalents thereof. Examples of absorbable materials include homopolymers and copolymers of lactide, glycolide, trimethylene carbonate, caprolactone, and p-dioxanone and blends thereof. Of particular utility are the following two blends:

(1) the blend of poly(p-dioxanone) and a lactide/glycolide copolymer, as disclosed in U.S. Pat. No. 4,646,741 which is incorporated by reference.

(2) the glycolide-rich blend of two or more polymers, one polymer being a high lactide content polymer, and the other being a high glycolide content disclosed in U.S. Pat. No. 4,889,119 which is incorporated by reference.

The tacks may also be made from conventional non-absorbable, biocompatible materials including stainless steel, titanium, polymers, composites and the like and equivalents thereof.

The following example is illustrative of the principals of practice of the present invention, although not limited thereto.

EXAMPLE I

A patient is prepared for surgery using conventional surgical preparatory techniques. The patient is anesthetized with a sufficient dose of a conventional anaesthesia to induce an effective anaesthetized state. An incision is made into the patient's abdominal cavity in order to access the site of an inguinal hernia using conventional surgical techniques. After the site of the inguinal hernia is prepared using conventional surgical techniques, a piece of a conventional, biocompatible surgical mesh is placed over the site of the inguinal hernia. Absorbable surgical tacks 10 of the present invention are applied by grasping the tacks 10 with an appropriate surgical grasping instrument and placing the tacks 10 into position proximal to the tissue to be fastened. The tacks 10 are made from a conventional absorbable polymeric material. The piercing points 58 of the spiral members 50 are positioned substantially perpendicular to the surface of the tissue. The tack 10 is then pushed distally through the mesh until the tip 58 pierces the tissue. The tack 10 is then rotated which causes it to move distally into the tissue until the bottom surface 40 of the base member 20 contacts the mesh.

After the mesh is secured by using a sufficient number of tacks 10 to effectively affix the mesh, for example about fifteen, the inguinal hernia procedure is completed in a conventional manner and the incision in the wall of the abdominal cavity is closed using conventional surgical sutures. The surgical tacks 10 maintain the surgical mesh over the site of the inguinal hernia and are absorbed by the patient's body over time.

Although this invention has been shown and described with respect to detailed embodiments thereof, it will be understood by those skilled in the art that various changes in form and detail thereof may be made without departing from the spirit and scope of the claimed invention.

What is claimed is:

1. A tack for use in a surgical procedure, the tack comprising:

a base member having a top surface and a bottom surface;

a spiral member extending from the bottom of the base member, said spiral member having at least one outer edge, the spiral member having a distal end, wherein the spiral member forms a spiral, said spiral comprising at least one coil, a longitudinal axis and an interior passage, wherein the spiral member has a substantially triangular cross-section with three outer edges; and, piercing means extending from the distal end of the spiral member.

2. The tack of claim 1 wherein the base member has a polygonal configuration.

* * * * *